United States Patent
Kaiser et al.

Patent Number: 5,613,938
Date of Patent: Mar. 25, 1997

[54] DIGITAL RETRACTOR

[75] Inventors: Susan Kaiser; Jill M. Rabin; Phyllis A. Shaw, all of New York, N.Y.

[73] Assignee: Mount Sinai School of Medicine of The City University of New York, New York, N.Y.

[21] Appl. No.: 450,629

[22] Filed: May 25, 1995

[51] Int. Cl.⁶ ....................................................... A61B 1/22
[52] U.S. Cl. ........................... 600/201; 600/210; 600/226; 602/22; 2/21
[58] Field of Search ..................................... 600/201, 206, 600/210, 213, 226; 601/40; 602/20–22; 20/16, 20, 21; 473/61, 62; 482/48

[56] References Cited

U.S. PATENT DOCUMENTS

| 48,354 | 6/1865 | Asmus | 2/21 |
|---|---|---|---|
| 69,258 | 9/1867 | Sechrist | 2/20 |
| 1,442,827 | 1/1923 | Richardson | 2/21 |
| 1,601,035 | 7/1925 | Nauth | 600/226 |
| 1,817,212 | 5/1928 | Siebrandt | 602/21 |
| 2,476,518 | 3/1946 | Underwood | 482/48 |
| 2,634,976 | 4/1950 | Mock | 482/48 |
| 3,038,723 | 11/1961 | Bergendorf | 473/61 |
| 3,729,006 | 4/1973 | Wilder et al. | 600/210 |
| 3,938,510 | 2/1976 | Gerber | 602/22 |
| 4,204,533 | 5/1980 | Forster et al. | 602/22 |
| 4,942,626 | 7/1990 | Stern et al. | 2/21 |
| 5,070,543 | 12/1991 | Beck | 2/21 |
| 5,295,948 | 3/1994 | Gray | 602/21 |
| 5,345,608 | 9/1994 | Mergens et al. | 2/16 |

Primary Examiner—Richard J. Apley
Assistant Examiner—Beverly M. Flanagan
Attorney, Agent, or Firm—Brumbaugh, Graves, Donohue & Raymond

[57] ABSTRACT

There is provided according to the invention a digital retractor to protect index finger, palm and thumb of the non-dominant hand of the surgeon during surgery, where the non-dominant hand is used to retract or position tissue. The retractor comprises a curved base plate which fits against the palmar surface of the index finger and extends toward the thumb, and includes one or two rings attached to the base plate through which the surgeon's index finger, and optionally also the long finger, are poised and positioned.

9 Claims, 2 Drawing Sheets

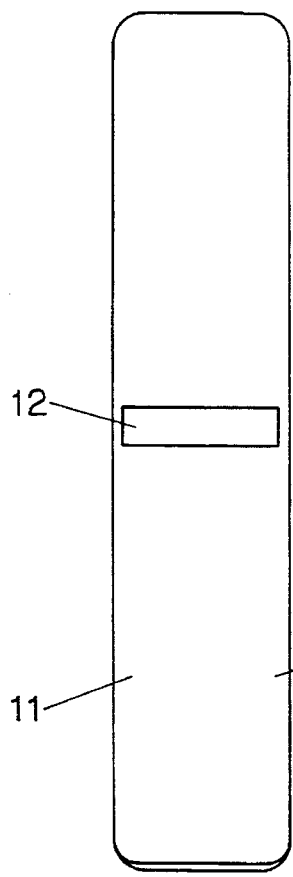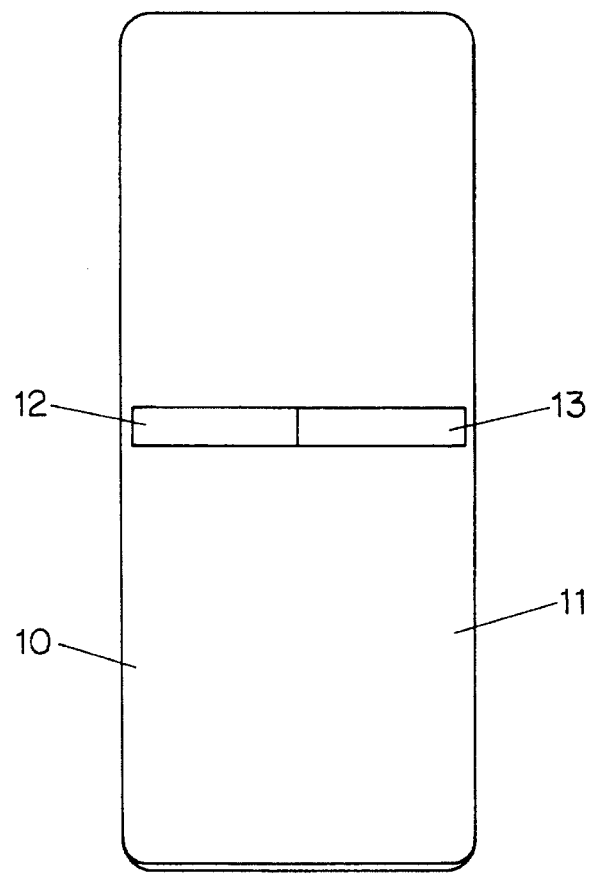
FIG. 1  FIG. 2
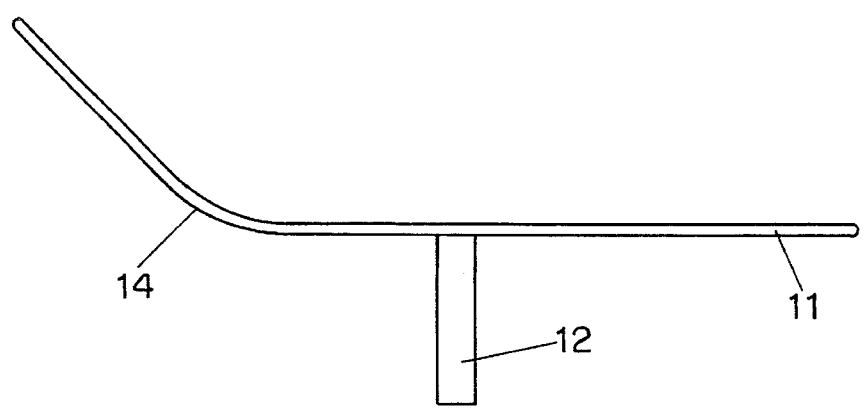
FIG. 3

# DIGITAL RETRACTOR

BACKGROUND OF THE INVENTION

Various surgical procedures require the use of both hands; i.e., the dominant hand for incising or suturing, and the non-dominant hand for retracting tissue to provide physical or visual access. The use of the non-dominant hand in close proximity to sharp surgical instruments such as needles and scalpels presents the danger of injury to the hand. Cuts and punctures not only pose a danger in and of themselves, but present the often more serious risk of infection, including infection with HIV.

The risk of injury to the surgeon's non-dominant hand is notably present during wound closure, particularly when the non-dominant hand is used to elevate the fascia of the abdominal wall during the placement of sutures. This danger is increased by the fact it is often necessary to exert considerable force to elevate the facia, while at the same time inserting a needle from the opposite side of the fascia toward the underlying non-dominant hand.

SUMMARY OF THE INVENTION

According to the invention, there is provided a digital retractor designed to protect the palmar surfaces of the surgeon's fingers as well as the patient's tissues during wound closure. Specifically, the retractor would protect the index and long fingers of the surgeon's non-dominant hand while it is being used to elevate the fascia of the abdominal wall during placement of sutures.

The digital retractor according to the invention comprises a relatively flat strip of hard material with one or two rings welded to the underside of the strip. The surgeon inserts the index finger into the ring such that the flat strip is caused to rest against the palmar surface of the index finger. A portion of the strip also extends toward and partially along the palmar surface of the thumb. In order to conform to the natural bend of the thumb relative to the index finger, the strip is curved approximately 45° at one end remote from the ring.

When in use, i.e., with the index finger inserted into the ring and the strip thereby positioned against the palmar surface of the index finger and thumb, the retractor provides tactile feedback during placement of sutures without endangering the surgeon's hand. It is particularly useful in closing small abdominal wounds. For larger wounds, it reduces the heavy labor of retracting the abdominal wall, necessary to provide direct vision of its interior surface. As long as the retractor is held firmly against the fascia, it will not readily slip, and loops of bowel will not be adjacent to the fascia being sutured. A needle may safely be passed through the fascia from the outside or the inside, as long as it touches the superior surface of the retractor while on the abdominal side of the fascia. The surgeon's finger(s) can easily be inserted into or removed from the ring of the retractor.

The device is intended to be used as described above by any surgeons who close abdominal wall wounds, including but not restricted to general and laparoscopic surgeons, gynecologists, and urologists. It could also be used in any situation where one or two fingers are used to retract tissue or other material in the presence of sharp instruments, as in oral surgery or veterinary surgery, or even shoemaking or fabric cutting.

BRIEF DESCRIPTION OF THE DRAWINGS

The retractor according to the invention is further described below with reference to the following drawings, wherein:

FIG. 1 is a bottom plan view of a single finger retractor according to the invention;

FIG. 2 is a bottom plan view of a double finger retractor according to the invention;

FIG. 3 is a side plan view of the retractors of FIGS. 1 and 2;

DESCRIPTION OF THE PREFERRED EMBODIMENTS

The retractor according to the invention may be made for use with the index finger alone, or with the index and long finger together. Looking to FIG. 1, the retractor 10 includes a base plate 11 comprised of a hard material that will resist penetration by a scalpel or needle.

This material may be metal, e.g., steel, stainless steel, or aluminum, or plastic or some other molded material. The material should be sterilizable, although it is also contemplated that retractors according to the invention may be disposable.

The base plate 11 has attached thereto one or possibly two rings 12, 13. If the retractor is metal, the rings may be welded or otherwise attached to the base plate. If the retractor is plastic, the base plate and ring(s) may be molded as a single unit.

In order to conform to the natural bend or angle formed between the thumb and index finger, the base plate preferably is curved upwardly and away from the ring side at one end of the base plate, as depicted in FIG. 3. While the angle formed by the bend depicted in FIG. 3 is approximately 45°, it may be varied to suit the preference of the user.

The base plate is contemplated as being a strip approximately 12 cm×2.5 cm (for one finger) or 12 cm×5 cm (for two fingers together). These dimensions may be altered to suit the user(s). The ring diameter, typically about 2.5 cm, may also be varied, as can the location of the bend 14, which is typically about 3 cm from one end of the base plate 11.

Figure 4:
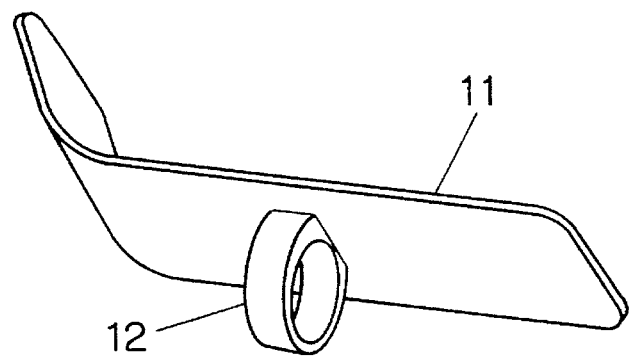
FIG. 4 is a perspective view of the retractor of FIG. 1.
Figure 5:
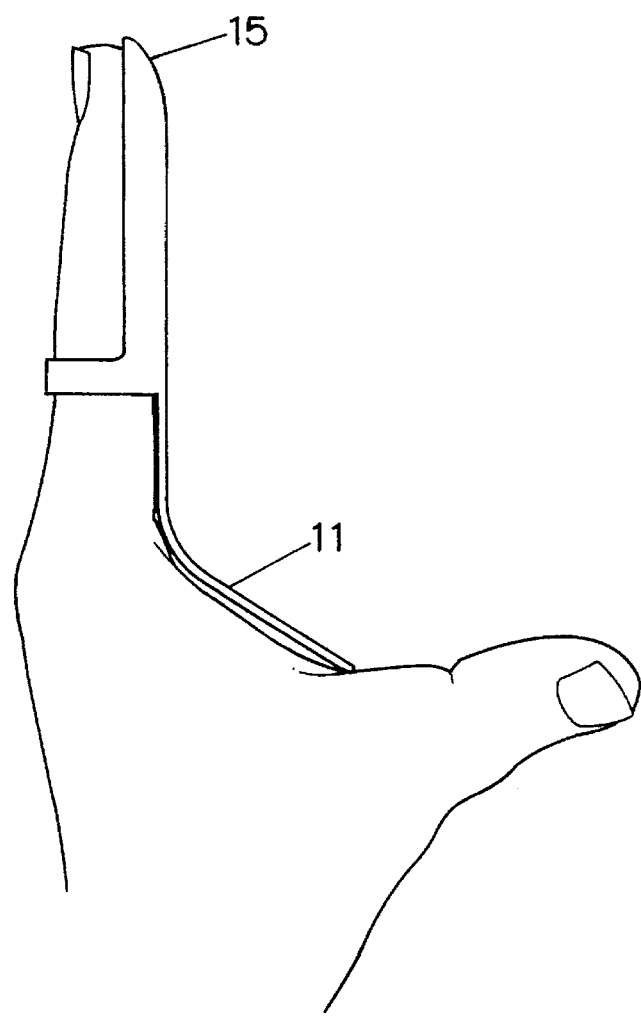
FIG. 5 is a side view of the retractor of FIG. 4 in conjunction with the left hand.

As shown in FIG. 5, in use the surgeon's gloved finger (or fingers) is inserted through the ring on the underside of the retractor. The hand and retractor are inserted between the abdominal wall fascia and the viscera, and the hand elevated so that the retractor is pressed firmly against the underside of the fascia. The curve fits in the palm of the hand, while the flat surface extends to the fingertip. The curve protects the palm and thumb and at the same time prevents the device from slipping into the abdominal cavity.

The retractor also may be shaped to conform to the finger and hand, e.g., by providing side-to-side concave curvature of the ring side surface of the base plate and/or by shaping the finger end of the base plate to extend beyond and at least partially up and around the fingertip, both as shown in FIG. 5 at the finger end 15 of the base plate 11. The concave curvature may extend along the entire length of the base plate so as to conform to the palmar surface of the palm and thumb.

The invention further includes the method, as described above, of using the retractor during surgery to retract and position patient tissue.

We claim:

1. A method of performing a surgical procedure on the abdomen of a patient, said method including the step of providing a retractor, said retractor comprising an elongated base plate having a proximal end, a distal end, lateral edges extending between the proximal and distal ends, and an upper surface adapted to fit against at least the palmar surface of the surgeon's index finger, and at least one ring attached to said surface of the base plate, said method further including the steps of inserting the index finger of a surgeon's non-dominant hand through said ring such that the upper surface of the retractor fits against said palmar surface, inserting the hand and retractor between the abdominal wall fascia and the viscera and elevating the hand so as to cause the retractor to be pressed against the underside of the viscera, thereby using the retractor to retract and position tissue of a patient during said surgical procedure.

2. A method according to claim 1, wherein the base plate is adapted to extend along at least a portion of the palmar surface of the user's palm, the base plate being curved at the proximal end downwardly and away from the upper surface so as to conform to the natural angle between the palmar surface of the index finger and palmar surface of the thumb.

3. A method according to claim 2, wherein the curve forms an angle of about 135° between the respective ends of the base plate.

4. A method according to claim 2, wherein the upper surface of the base plate is concave between said lateral edges to conform to the palmar surface of the index finger.

5. A method according to claim 4, wherein the concave upper surface of the base plate extends substantially along the entire length of the base plate.

6. A method according to claim 1, wherein the base plate is adapted to contact the palmar surfaces of the user's index finger and long finger, and including a second ring laterally adjacent the first one ring and adapted to receive the long finger of the user.

7. A method according to claim 2, wherein the distal end of the base plate extends at least partially up and around the index fingertip.

8. A method according to any one of claims 1–7, said retractor being comprised of metal or plastic.

9. A method according to claim 8, said retractor being comprised of at least one of steel, stainless steel, aluminum or plastic.

* * * * *